United States Patent
Galbierz et al.

(10) Patent No.: US 10,959,885 B2
(45) Date of Patent: Mar. 30, 2021

(54) WOUND EXPOSURE DEVICE FOR USE WITH PATIENTS HAVING EXCESSIVE AND/OR REDUNDANT TISSUE AND METHOD OF USE

(71) Applicant: GSQUARED MEDICAL LLC, Brentwood, TN (US)

(72) Inventors: Thomas R. Galbierz, Brentwood, TN (US); Michael A. Galbierz, St. Louis, MO (US)

(73) Assignee: GSQUARED MEDICAL LLC, Brentwood, TN (US)

( * ) Notice: Subject to any disclaimer, the term of this patent is extended or adjusted under 35 U.S.C. 154(b) by 568 days.

(21) Appl. No.: 15/543,474

(22) PCT Filed: Jan. 14, 2016

(86) PCT No.: PCT/US2016/013404
§ 371 (c)(1),
(2) Date: Jul. 13, 2017

(87) PCT Pub. No.: WO2016/122892
PCT Pub. Date: Aug. 4, 2016

(65) Prior Publication Data
US 2018/0008477 A1    Jan. 11, 2018

Related U.S. Application Data

(60) Provisional application No. 62/108,339, filed on Jan. 27, 2015.

(51) Int. Cl.
*A61F 13/14* (2006.01)
*A61F 13/02* (2006.01)
(Continued)

(52) U.S. Cl.
CPC .............. *A61F 13/148* (2013.01); *A61F 13/02* (2013.01); *A61B 1/32* (2013.01); *A61B 17/02* (2013.01)

(58) Field of Classification Search
CPC .............. A61F 15/00; A41F 9/00; A41C 3/065
(Continued)

(56) References Cited

U.S. PATENT DOCUMENTS 3,701,755 A * 10/1972 Furusawa ............ C08G 63/672
                                                   528/301
3,930,497 A *  1/1976 Krebs ..................... A61B 46/00
                                                   128/853
(Continued)

FOREIGN PATENT DOCUMENTS

WO      9707760 A1    3/1997
WO   2014120746 A1    8/2014
(Continued)

OTHER PUBLICATIONS

Extended European Search Report from corresponding EP Application No. 17803333.8 dated Dec. 16, 2019.
(Continued)

*Primary Examiner* — Ophelia A Hawthorne
*Assistant Examiner* — Caitlin A Carreiro
(74) *Attorney, Agent, or Firm* — Sandberg Phoenix & von Gontard, P.C.

(57) ABSTRACT

A wound exposure device is disclosed that can be applied to a patient having excessive or redundant tissue (i.e., a panniculus) to retain the excessive or redundant tissue away from (off of) a wound to allow air so that the excessive or redundant tissue will not cover the wound while the wound is healing. The wound exposure device is wearable and highly conformable when applied to a patient to support/hold/retract redundant and/or excessive tissue off or away (Continued)

from a wound site for extended periods of time. The ability to wear the wound exposure device for extended periods of time facilitates better healing of wounds which would otherwise be covered by the redundant flesh.

46 Claims, 9 Drawing Sheets

(51) Int. Cl.
*A61B 1/32* (2006.01)
*A61B 17/02* (2006.01)

(58) Field of Classification Search
USPC ..... 128/845, 849, 851; 600/201–246; 2/310, 2/311, 312, 309
See application file for complete search history.

(56) References Cited

U.S. PATENT DOCUMENTS

| | | | |
|---|---|---|---|
| 5,381,802 A | 1/1995 | Schwartzenfeld | |
| 5,891,077 A | 4/1999 | Gilman et al. | |
| 6,541,089 B1 | 4/2003 | Hamerski et al. | |
| 6,666,747 B1 * | 12/2003 | Buntz | A41C 3/065 |
| | | | 424/400 |
| 7,473,158 B2 * | 1/2009 | Horton | A61K 9/7007 |
| | | | 450/1 |
| 2006/0137262 A1 | 6/2006 | Crowder-Moore et al. | |
| 2009/0264709 A1 | 10/2009 | Blurton et al. | |
| 2011/0111240 A1 * | 5/2011 | Yuan | C09J 133/08 |
| | | | 428/480 |
| 2011/0213322 A1 * | 9/2011 | Cramer | A61F 5/443 |
| | | | 604/344 |
| 2012/0029295 A1 | 2/2012 | Long Sharps et al. | |
| 2016/0007980 A1 | 1/2016 | Galbierz et al. | |
| 2019/0336233 A1 | 11/2019 | Galbierz et al. | |

FOREIGN PATENT DOCUMENTS

| | | | | |
|---|---|---|---|---|
| WO | 20140120746 A1 | | 8/2014 | |
| WO | WO-2014120746 A1 * | | 8/2014 | ............ A61B 46/00 |
| WO | 2015052288 A1 | | 4/2015 | |

OTHER PUBLICATIONS

International Preliminary Report on Patentability for corresponding PCT/US2016/013404 dated Aug. 23, 2017.
International Search Report corresponding to PCT/US2016/013404, dated Jun. 3, 2016.
Written Opinion corresponding to PCT/US2016/013404, dated Jun. 3, 2016.

* cited by examiner

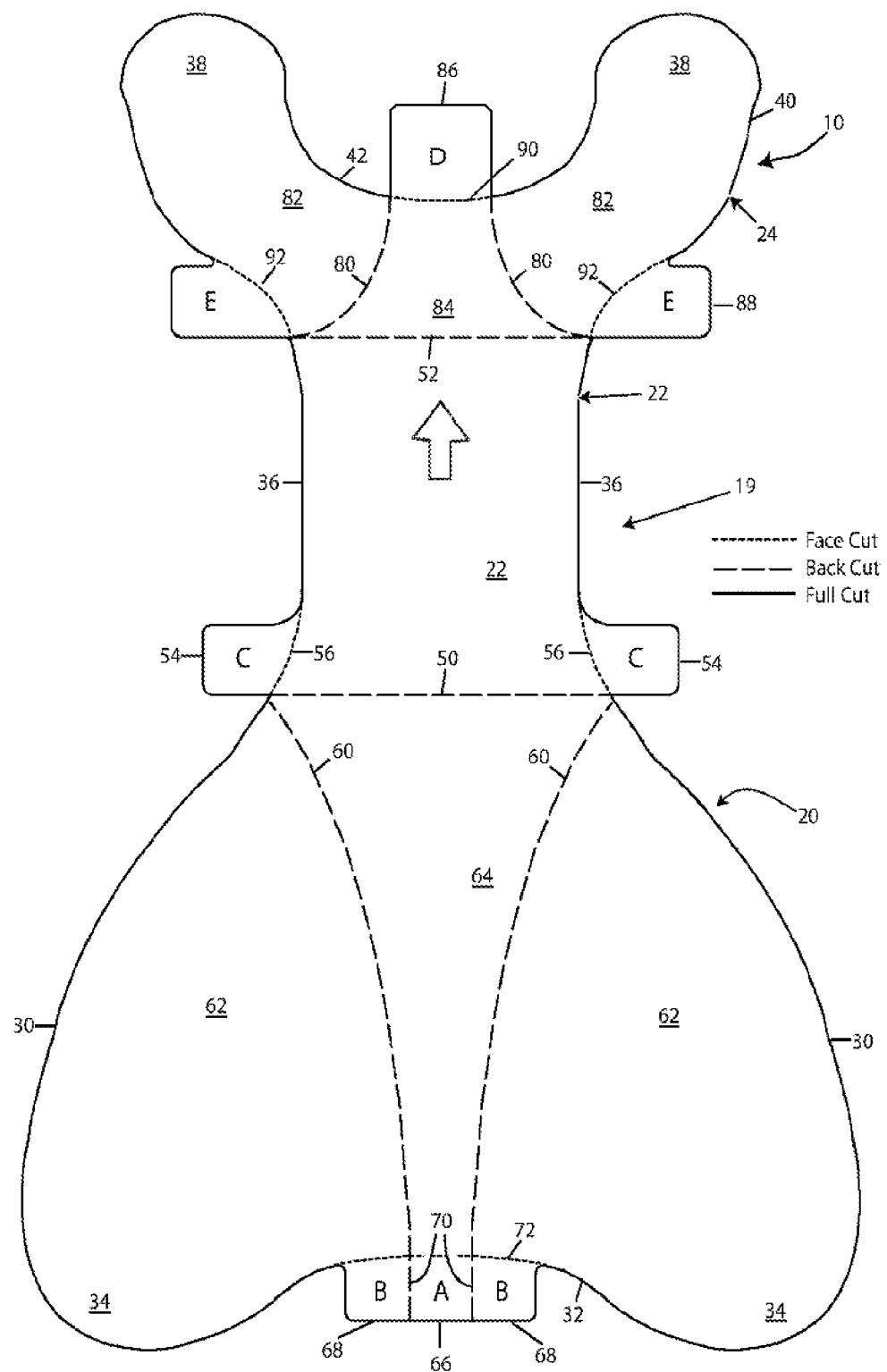
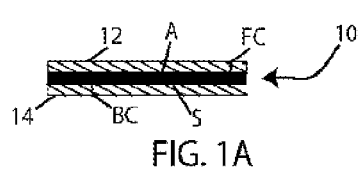
FIG. 1
FIG. 1A

WOUND EXPOSURE DEVICE FOR USE WITH PATIENTS HAVING EXCESSIVE AND/OR REDUNDANT TISSUE AND METHOD OF USE

RELATED APPLICATIONS

This application is the US National Stage under 35 U.S.C. § 371 of International App. No. PCT/US2016/013404 filed Jan. 14, 2016, which claims priority to U.S. App. No. 62/108,339 filed Jan. 27, 2015 and entitled "Wound Exposure Device For Use With Patients Having Excessive And/Or Redundant Tissue And Method Of Use," which is incorporated herein by reference. In addition, this application is related to International App. No. PCT/US2014/013563 (published as WO2014/120746) having an International filing date of Jan. 29, 2014, which is entitled "Retractor/Stabilizer For Excessive And/Or Redundant Tissue And Method Of Use," and which is incorporated herein by reference.

STATEMENT REGARDING FEDERALLY SPONSORED RESEARCH OR DEVELOPMENT

Not Applicable.

BACKGROUND OF THE INVENTION

This application relates to an engineered, adaptable, predictable supporting device/system that can be used to displace, reposition, retract, secure and/or stabilize excessive and/or redundant tissue (such as adipose tissue, breast tissue, panniculus tissue, etc.) for an extended period of time to maintain such excess tissue away from a wound (such as a surgical incision) to facilitate healing. The device can be termed a wound exposure/wound healing assist device. A significant portion of surgical patients present to the operating room with a BMI (Body Mass Index) over 30. People with a BMI over 30 are considered to be obese, and will commonly have a panniculus (or layer/apron of fat which hangs from the abdomen). Depending on how obese the individual is, the panniculus (or adipose layer or fatty layer) can extend to the pubic hair line (in smaller panniculi) or to the knees and beyond (in very large panniculi). This situation has been arising more frequently in recent years due to a greater number of people being morbidly obese than in years past. Many of these individuals accumulate a large mass of adipose (fatty tissue) in the lower abdominal area producing a panniculus (apron of fat) that hangs, depending on its size, over the abdominal wounds, and over the groin, genital area and upper thighs.

Patients with such large BMIs require the clinical staff to manage excessive amounts of adipose (or fatty tissue), skin and other tissues (i.e., collectively, the panniculus). There is currently no practical device available to manage (displace, reposition, retract, secure and/or stabilize) the excess or redundant tissue so that it is held away from the surgical site for an extended period once the surgery has been completed. Without such a device, the excessive or redundant tissue will cover the surgical incision which will impair and complicate the ability for the surgical incision and/or wound to heal correctly and expeditiously. PCT App. Pub. No. WO2014/120746, which is incorporated herein by reference, discloses a retractor system which can be used to retain excessive or redundant tissue away from a surgical site. However, the retractor system of WO2014/120746 was initially designed for use during a surgical procedure.

SUMMARY

Briefly stated, a wound exposure device is disclosed that can be applied to a patient having excessive or redundant tissue (i.e., a panniculus) to retain the excessive or redundant tissue away from (off of) a wound so that the excessive or redundant tissue will not cover the wound while the wound is healing. The wound exposure device is wearable and highly conformable when applied to a patient to support/hold/retract redundant and/or excessive tissue off of, or away from, a wound site for extended periods of time. The ability to wear the wound exposure device for extended periods of time facilitates healing of wounds.

In accordance with an aspect of the wound exposure device, the wound exposure device comprises an upper portion defining a yoke, a middle portion, and a bottom portion. At least the yoke and bottom portion comprise a top layer and a backing layer. The top layer has an adhesive applied to a surface of the top layer facing the backing layer to removably adhere the top layer and backing layer together. At least the middle portion is made from a stretchable material which has at least a 50% elongation.

At least one tab is associated with each of the top and bottom portions. Each of the tabs is defined in part by a face cut in the top layer which separates the top layer in the area of the tab from the top layer in the area of the body, such that when the tab is pulled away from the top layer, a backing panel associated with the tab is removed from the top layer.

In accordance with one aspect, the wound exposure device can be formed from a single sheet of two-ply material. In this instance, the entire top ply or layer is preferably stretchable.

In accordance with another aspect, the wound exposure device comprises an upper piece defining the yoke and a bottom piece defining the bottom portion. In one variation, the wound exposure device is a two-piece assembly, wherein the upper piece defines a lower part of the middle portion and the bottom piece defines an upper part of the middle portion. In another variation, wound exposure device is a three-piece assembly, which includes a middle piece defining at least a top part of the middle portion. In this variation, the top and bottom pieces need not be stretchable, or can be less stretchable than the stretchable middle piece. Additionally, in this variation, the middle piece can be formed from a one-ply material which is non-adhesive.

In accordance with a further aspect of the wound exposure device, the wound exposure device is formed from a single sheet of two-ply material having a top layer and a backing layer. The top layer has an adhesive applied to a surface of the top layer facing the backing layer to removably adhere the top layer and backing layer together. The top layer is made from a stretchable material and the backing layer being made from a material which is substantially not stretchable. The wound exposure device comprises:

a body defining a bottom portion, a central portion and an upper portion, the portions being separated from each other by upper and lower back cuts in the backing layer which divide the backing layer into a lower portion backing panel, a central portion backing panel and an upper portion backing panel; and at least one tab associated with each portion of the body; each of the tabs being defined in part by a face cut in the top layer which separates the top layer in the area of the tab from the top layer in the area of the body, such that when the tab is pulled away from the top layer, a backing panel associated with the tab is removed from the top layer.

Whether the wound exposure device is a one-piece product or a multi-piece product, it can include the following characteristics, constructions, or properties in any desired combination.

The top portion is generally U-shaped or yoke-shaped, and defines arms extending from a central portion of the yoke. The arms of the yoke are sized to extend around a patient's neck to the patient's scapula when the wound extractor is applied to the patient.

The tabs can be outboard tabs and extend from the body of the wound exposure device. Alternatively, the tabs can be inboard tabs, which have outer edges that are generally flush with the perimeter of the body.

The lower back cut which separates the lower portion from the middle portion can be either a generally straight line or an upwardly extending generally arcuate line.

In accordance with an aspect of the wound exposure device, the lower portion backing panel has at least a first back cut extending from the lower back cut to a bottom edge of the body to divide the lower portion backing panel into at least first and second backing layer panels. In this instance, a tab is associated with each of the first and second backing layer panels.

The lower portion can include a second back cut extending from the lower back cut to the bottom edge to define a third panel. In this instance, two of the panels are side panels and one the panels is a central panel between the side panels. A tab is associated with each of the three panels. In this variation, the back cuts in the lower portion can extend from ends of the lower back cut to a point on the lower edge proximate the center of the lower edge, such that the central panel has an upper edge defined by the lower back cut which is longer than a lower edge defined by the bottom edge of the body.

The upper portion backing panel can be provided with at least a first upper portion back cut extending from the upper back cut to an upper edge of the body to divide the upper portion backing panel into first and second upper portion backing layer panels. A tab is preferably associated with each of the first and second upper portion backing layer panels. The upper portion can further include a second upper portion back cut extending from the upper back cut to the upper edge of the body to define a third upper portion panel. A tab is preferably also associated with the upper portion central panel. In the three panel upper portion variation, two of the upper portion panels define upper portion side panels or arm panels and one of the upper portion panels defines an upper portion central panel between the upper portion side panels or arm panels.

The upper portion back cuts preferably extend from ends of the upper back cut (which separates the body middle portion from the body upper or yoke portion) to a point on the upper edge of the body proximate the center of the upper edge, such that the upper panel central panel has an upper edge defined by the upper edge of the body which is shorter than a lower edge defined by the upper cut in the backing layer.

In accordance with an aspect of wound exposure device, the top layer, or the stretchable portion of the wound exposure device, is comprised of a material that has an elongation factor of at least 50% in the machine direction. The stretchable material can have an elongation factor of up to 500% in the machine direction of the material. The stretchable material can be a thermoplastic elastomer, such as a polyester and/or polyurethane. The stretchable material can also include Spandex or Lycra fibers. In the three-piece version, the middle piece stretchable material can include stretchable fibers or materials mixed with non-stretchable or less-stretchable fibers or material to provide a material that is more comfortable to wear for longer durations.

In accordance with one aspect of the wound exposure device, the top layer (or the material applied to the patient) has thickness of about 1 mil to about 5 mils.

In accordance with another aspect of the wound exposure device, the top layer (or the material applied to the patient) has a machine direction which extends from top-to-bottom of the device.

In accordance with an aspect of the wound exposure device, the top layer (or the material applied to the patient) has a machine direction which extends from side-to-side of the device.

In accordance with an aspect of the wound exposure device, the adhesive used to apply the device to a patient has an adhesive strength sufficiently low so as to substantially prevent trauma to human skin when the device is removed from human skin. The adhesive can, for example, have a strength of about 10 oz/in to about 50 oz/in.

In accordance with another aspect of the wound exposure device, the wound exposure device can include an arm extending from each of the opposite sides of the body. These arms can each comprise a first arm portion which extends in a direction generally parallel to the machine direction of the material of the top layer to be stretchable to the full extent of the stretchability of the top layer and a second arm portion which is not generally parallel to the machine direction of material of the top layer. The backing layer of the arm second portion can be separated from the backing layer of the arm first portion by a back cut; and a tab can be associated with the backing layer of the arm second portion to facilitate removal of the backing layer of the arm second portion. In a preferred embodiment, no tab is associated with the arm first portion; however, a tab can be provided for the arm first portion if desired.

In accordance with an aspect of the wound exposure device, the arm can include wings extending along opposite sides of at least a portion of each of the arms to provide a segment of increased width for each the arm.

A method of applying the wound exposure device to a patient to support and maintain redundant and/or excess flesh (such as a panniculus) away from a wound (such as an incision) to facilitate healing of the wound is also disclosed. The method comprises:
 a) manually retracting the redundant/excess tissue away from the wound and in a cephalad direction;
 b) removing the backing layer from the bottom portion of the film and applying the bottom portion of the film to the patient's redundant/excess tissue;
 c) removing the backing layer from the central portion of the top layer after the bottom portion has been applied to the patient;
 d) while the backing layer is still adhered to the top portion of the retainer and while still manually retracting the redundant/excess tissue, stretching the middle portion until a top edge of the wound exposure device is proximate the patient's clavicle or jugular notch and then securing the central portion of the wound exposure device to the patient;
 e) removing the backing layer from the upper portion of the wound exposure device and applying the upper panel of the film to the patient.

In accordance with an aspect of the method, the step (b) of removing the backing layer from the bottom portion of the wound exposure device comprises:

b1) removing a first portion of the lower panel backing layer to expose a positioning area of the top layer bottom portion and adhering this positioning area to the patient's redundant/excess tissue; and b2) then removing the remainder of the bottom portion backing layer to expose the adhesive surface of the top layer of the remainder of the bottom portion backing layer and adhering the remainder of the bottom portion of the top layer to the patient's redundant/excess tissue.

In the variation of the wound exposure device in which the bottom portion of the body is divided into three parts, the first portion of the lower panel backing layer that is removed in step (b1) exposes the adhesive surface of the top layer in a central area of the bottom portion of the top layer; the step of removing the remainder of the bottom portion backing layer comprise (1) removing a first of the backing layer side panels and adhering the top layer corresponding to the first of the backing layer side panels to the patient's redundant/excess tissue and (2) removing a second of the backing layer side panels and adhering the top layer corresponding to the second of the backing layer side panels to the patient's redundant/excess tissue.

In accordance with an aspect of the method, the step of removing the backing layer from the top portion of the wound exposure device comprises:

e1) removing a first part of the upper portion backing layer to expose a positioning area of the top layer upper portion and adhering this positioning area to the patient proximate the patient's clavicle or jugular notch and then securing the central panel of the wound exposure device to the patient; and e2) then removing the remainder of the upper portion backing layer to expose the adhesive surface of the top layer of the remainder of the upper portion backing layer and adhering the remainder of the upper portion of the top layer to the patient.

In the variation of the wound exposure device in which the upper portion includes three sections, the first portion of the upper portion backing layer that is removed in step (e1) exposes a portion of the adhesive surface of the top layer in a central area of the upper portion of the top layer; the step of removing the remainder of the upper portion backing layer comprises (1) removing a first of the upper portion backing layer side panels and adhering the top layer corresponding to the first of the backing layer side panels to the patient, and (2) removing a second of the upper portion backing layer side panels and adhering the top layer corresponding to the second of the upper panel backing layer side panels to the patient.

In the variation of the wound exposure device comprising arms, the method further comprises a step (f) of adhering the top layer of each of the arms to the patient such that the arms extend along at least a portion of the patient's back and over a shoulder of the patient, such that the arm second portion can be adhered to the top portion of the body of the wound exposure device.

This step (f) of adhering the top layer of each of the arms to the patient can comprise:

(f1) removing the backing panel from the arm first portion and stretching the arm first portion until the arm second portion can be positioned to be adhered to the upper portion of the body of the wound exposure device with the arm first portion extending along at least a portion of the patient's back;

(f2) adhering the arm first portion to the patient;

(f3) removing the backing layer from the arm second portion; and (f4) adhering the arm second portion to the patient and to the upper portion of the body of the wound exposure device.

In accordance with an aspect of the method, step of stretching the arm first portion comprises stretching the arm such that the arm remains on one side of the patient's body.

In accordance with an alternate aspect of the method, the step of stretching the arm first portion comprises stretching the arm such that the arm cross behind the patient such that each arm extends diagonally upwardly and over the opposite shoulder.

BRIEF DESCRIPTION OF THE DRAWINGS

FIG. 1 is a plan view of a wound exposure device;

FIG. 1A is a schematic cross-section of the wound exposure device;

Corresponding reference numerals will be used throughout the several figures of the drawings.

DETAILED DESCRIPTION OF THE INVENTION

Figure 2:
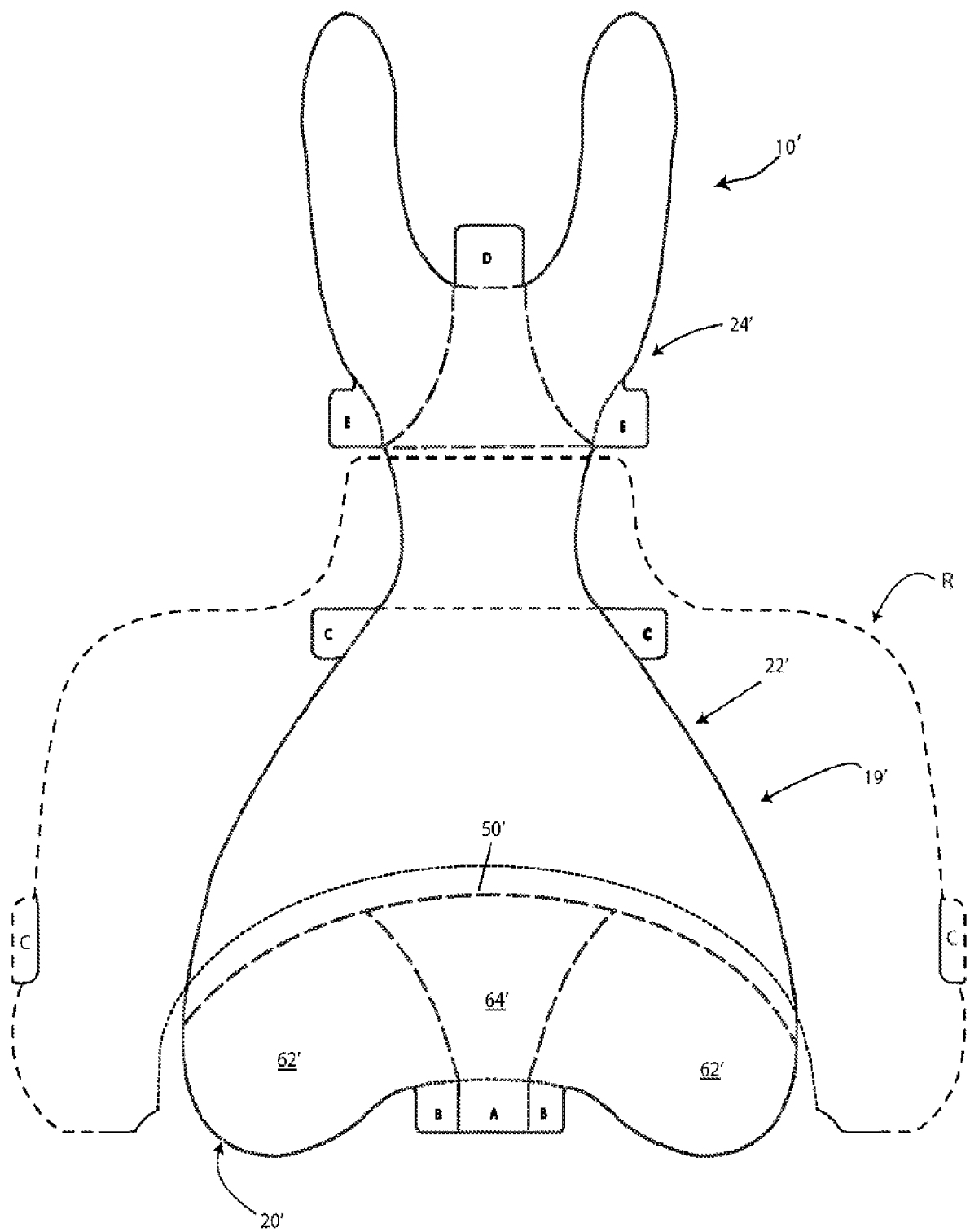
FIG. 2 is a plan view of a variation of the wound exposure device with the wound exposure device being shown in connection with a retractor from WO2014/120746.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction, the arrangements of components, utilization of specifications and/or the materials set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

A wound care or exposure device is shown in the figures which can be used to restrain/secure/hold, etc., excessive tissue away from a wound (such as a surgical incision) sufficiently to allow for better healing of the wound. The device complements wound healing by maintaining a uniform radius of retraction. It assists and enables in the approximation of the margins of the wound to facilitate wound closure, which will reduce scarring and potential wound complications. The use of this device also assists in the re-approximation of the margins of the wound in the case of post-operative rupture of the wound or in the need to re-suture the incision line. This is accomplished due to the uniformity of the retraction, which, in the case of a secondary or tertiary wound closure, assists in the re-approximation of the margins of the wound.

The device allows the clinician better access to the wound site to inspect, evaluate, treat and apply dressings to the wound site without having to manipulate the patient's adipose tissue. It also allows for ambient air flow over the wound site, thereby reducing excessive moisture, and minimizing the environment suitable for microbial growth, to expedite wound healing and reduce potential wound complications. The device thus reduces (or altogether eliminates) the need for debridement, infection control, the use of antibiotics due to secondary infection from the wound site being covered by the excessive tissue. The device facilitates clinician's access to the wound, and promotes healing and monitoring of the wound. This device is preferably constructed from a material having high conformability and a sufficient moisture vapor transmission rate The device can be formed as a single piece device or as a multi-piece device. Preferred materials from which the device is made include polymer films available from 3M under product codes 9948 and 9832F, as well as woven substrates, that have an adhesive or co-adhesive. The combinations would maintain a moisture vapor transmission rate (MVTR), as well as physical characteristic properties.

A wound exposure device 10 is shown generally in FIG. 1 and in a schematic cross-section in FIG. 1A. The wound exposure device 10 comprises a top layer, film, or ply 12 and a bottom layer or ply 14. The top ply 12 has a surface which is coated with an adhesive A which removably holds the two plies together. The top ply 12 is preferably made from a sheet of flexible, breathable material which is stretchable in the cross-machine and in the machine direction. Preferably, the top ply or layer has an elongation of at least 50%, preferably at least 150%, and more preferably at least 500%. The top layer can be made from a polyethylene, for example. Alternatively, the top ply 12 can be formed from fibers which have a machine direction which renders the top ply stretchable. The bottom layer is preferably flexible, but not stretchable, and, for example, can be made from paper. The bottom layer can have a coating S, for example, of silicone, to facilitate separation of the bottom layer from the top layer such that the adhesive remains with the top layer.

By way of example, the wound exposure device 10 can be made from Conformable Breathable Incisable Tape 9948, which is available from 3M. Another acceptable tape is 3M's medical tape available under product number 9834. These tapes have a top layer formed from a polymer, such as a polyester or polyethylene film and a bottom layer formed from a silicone coated paper. The film is coated with an acrylate adhesive. The top layer is thin. In the 3M 9948 film, for example, the top layer is about 0.004" to about 0.005" (about 0.0.1 mm to about 0.13 mm), has a weight of about 0.13 lbs/ft$^2$, and an elongation of about 500%. In the 9834 film, the top layer is about 0.0008" (about 0.02 mm) thick, and has an elongation of about 500%. Further, the film is air permeable, but liquid impermeable. These features make the film more comfortable to the patient. Other films could also be used. The two noted films have the following properties:

|  | Property | |
| --- | --- | --- |
|  | 9834 Film | 9948 Film |
| Elongation | 500% | 500% |
| Minimum Tensile Strength | 3.5 lbs/in | 13.3 lbs/in |
| Typical Adhesion/stainless steel | 15 oz/in | 19 oz/in |
| Top Layer thickness | ~0.8 mil | ~4 to ~5 mils |

The wound exposure device 10 is formed from a monolithic sheet of material, and is formed, for example, in a die-cutting process. The sheet of material from which the wound exposure device is formed preferably has a machine direction, and the wound exposure device 10 is cut such that the machine direction extends in the top-to-bottom direction, rather than from a side-to-side direction, of the wound exposure device. As discussed below, this enables the top layer 12 of the wound exposure device to be stretched length-wise. Back cuts or back slices BC are formed in the backing layer 14, face cuts or slices FC are formed in the film or top layer 12 and full cuts extend through both the top and backing layers. To help distinguish the cuts in FIG. 1, the back cuts are shown as dashed lines (i.e., - - - ), the face cuts are shown as dotted lines (i.e., ●●●●●), and the full cuts are shown as solid lines (i.e., ------).

Turning to FIG. 1, the wound exposure device 10 defines a body 19 that can be divided into a lower portion 20, a center portion 22, and an upper portion 24. The lower portion has two generally convexly curved side edges 30 which curve around to define a bottom edge 32, such that the lower portion 20 defines a pair of lobes 34. The curvature of the bottom edge 32 corresponds generally to, or simulates the, curvature of a patient's abdomen and/or other anatomy of the patient.

The central portion 22 is generally rectangular and is defined by a pair of side edges 36 which continue from the side edges 30 of the lower panel 20.

Finally, the upper portion 24 is generally U-shaped, comprising a pair of side arms 38 defined by a convexly curved outer edge 40 and a concave, U-shaped upper edge 42. The outer edge 40 and upper edge 42 of the upper portion 24 are joined by a curved edge.

The central portion 22 is distinguished or separated from the lower portion 20 and upper portion 24 by a lower back cut line 50 and an upper back cut line 52, both of which are formed in the backing or bottom layer 14 of the wound exposure device. Tabs 54 (printed with the letter "C") extend from the bottom of the central portion 22. The tabs 54 thus have bottom edges that are even with (and are effectively a continuation of) the lower cut line 50. The tabs 54 are, in part, defined by face cuts 56 in the top layer 12 of the wound exposure device 10 which separate the top layer of the tabs 54 from the top layer of the body 19 of the wound exposure device. As will be described below, the C-tabs 54 can be bent away from (rearwardly of) the top layer 12 and are used to remove the backing layer from the central portion 22 of the body 19. Although the C-tabs 54 are level with the lower cut line 50, the C-tabs could be level with the upper cut line 52. The C-tabs could also be positioned midway along the central panel 22 of the wound exposure device, but such a positioning is less desirable. Further, the C-tabs 54 could be "internal" tabs, such as disclosed in our noted PCT Pub. No. WO2014/120746 in which the outer edges of the tabs are flush with the outer edge of the body, rather than tabs which extend from the edges of the central portion 22.

The lower portion 20 comprises a pair of back cuts 60 in the backing layer 14, each of which extends downwardly and inwardly from an end of the lower back cut 50 to the bottom edge 32 substantially inwardly of the side edges 30 of the lower portion 20. These two back cuts 60 divide the backing layer of the lower portion 20 into three lower portion panels: two lower portion outer panels 62 and a lower portion central panel 64. The back cuts 60 are shown to be curved, such that the central panel is generally anvil-shaped. That is, the central panel 64 is substantially narrower at the bottom edge 32 of the lower portion 20 than at the lower cut line 50 (at the top of the lower panel 20). The two back cuts 60 define generally concave edges for the central panel 64. As will be described below, the central area 64 of the top layer defines a positioning portion of the body lower portion 20 of the wound exposure device. Although it is preferred that the lower portion be divided into a center portion and two side portions, the lower portion could be provided with a single back cut, or even no back cut. In this latter instance, the lower panel would not include a separate positioning portion.

The bottom portion 20 includes an A-tab 66 at the bottom edge of the central panel 64 and a B-tab 68 at the bottom edge of each outer panel 62. Illustratively, the A-tab is between, and separated from, the B-tabs 68 by full cuts 70 which extend through both the top and bottom layers 12, 14 of the wound exposure device 10. The full cuts 70 are continuations of the back cuts 60. Additionally, face cuts separate the top layer of the tabs 66 and 68 from the top layers of their respective panels 64 and 62. Illustratively a single face cut 72 extends across all three tabs 66 and 68. The A-tab 66 is operable to remove the central backing panel 64 from the body top layer; and the two B-tabs 68 are operable to remove their respective side backing panels 62 from the body top layer. Although the A- and B-tabs are shown to be adjacent each other, the B-tabs could be spaced from the A-tab if desired. For example, the B-tabs could be positioned at the bottom of the lobs 34 or could be positioned along the side edge 30 (for example, just below the lower cut line 50 and C-tab 54).

The back cuts 60 which define or separate the three panels of the lower portion backing layer could be shaped such that they are straight (such that the central panel is generally trapezoidal) or they could be convexly curved. Alternatively, the back cuts 60 could be generally parallel to each other, such that the central section of the bottom portion is generally straight (or rectangular). Alternatively, a single curved back cut could be provided which would define an arced section at the bottom of the lower panel 20 of the wound exposure device. In this instance, the backing layer of the body lower portion would be divided into two panels—the curved or arced panel to expose the positioning area of the top layer and the remainder of the backing layer of the body bottom portion (which would surround the positioning panel).

The upper portion 24 of the wound exposure device includes two back cuts 80 which divide the back layer of the upper portion 24 into two side or arm panels 82 and a central panel 84. The back cuts 80 extend from the ends of the upper back cut 52 to a central portion of the upper edge 42. The back cuts 80 are illustratively shown to be inwardly curved or arced, giving the central panel 84 the general shape of a trapezoid, but having concave side edges. However, the back cuts 80 could be generally parallel, such that the central panel 84 is generally rectangular. Alternatively, a single arced back cut could be provided which forms an arc extending inwardly from the top edge 42 of the upper portion 24.

The upper portion 24 is provided with a D-tab 86 associated with the upper portion central panel 84 and an E-tab 88 associated with each of the side or arm panels 82. The D-tab 86 is positioned at the approximate center of the upper edge 42 of the upper portion 24, and is defined in part by a face cut 90 which separates the upper layer 12 of the tab 86 from the upper layer 12 of the upper section 84. Similarly, the E-tabs 88 are each defined in part by a face cut 92 which separates the upper layer 12 of the E-tabs 88 from the upper layer of the upper panel 24. As with the bottom portion 20, the top portion 24 could be provided with just one, or even no, back cuts, such that the upper portion backing layer would be removed in two pieces, or as one large piece. However, the division of the upper portion backing layer into three sections eases handling of the upper portion, and is thus preferred.

The wound exposure device 10 is formed with "external" or outboard tabs. That is, the tabs 54, 66, 68, 86 and 88 all extend from respective edges of the body of the wound exposure device. The wound exposure device could be formed with some, or all, of the tabs as inboard tabs, such that the outer edges of the tabs are flush with the outer edge of the body of the wound exposure device. Such inboard tabs are disclosed, for example, in our PCT Pub. No. WO2014/120746. In this instance, the tabs would not protrude from the body, as do the tabs which are shown in FIG. 1.

Application of the Wound Exposure Device to a Patient

Application of the wound exposure device 10 to a patient can be accomplished quickly and easily. As noted, the wound exposure device 10 is intended for use after surgery. Thus, before the wound exposure device 10 is applied to a patient, any retraction device (such as a wound exposure device made in accordance with our PCT Pub. No. WO2014/120746) that was used during the surgical procedure is removed. Application of the wound exposure device 10 will be described for use in retracting a panniculus after an abdominal surgery, although the wound exposure device 10 could be used to retract excess or redundant tissue after other procedures.

The wound exposure device 10 is applied to the patient when the patient is in a supine (and, optionally, a Trendelenburg) position. Once the retractor/stabilizer (such as the retractor/stabilizer disclosed in WO2014/120746, which is incorporated herein by reference) used during surgery has been removed, and the wound (incision) site has been cleaned and otherwise prepared, the wound exposure device 10 can be applied to the patient. Initially, the patient's panniculus is manually retracted in a cephalad direction (toward the patient's head). With the patient's panniculus (or adipose tissue) manually retracted, the bottom edge 32 of the wound exposure device 10 is positioned typically about 3 cm to about 5 cm above the incision line. The A-tab 66 is pulled downwardly to remove the lower portion central panel 64 of the backing layer from the top layer 12 of the wound exposure device. This exposes a window or portion of the adhesive of the film (or top layer) 12 in the central area 64 of the lower portion 20 of the wound exposure device. With the lower portion central panel 64 of the backing layer removed, the exposed portion of the film is applied (via the adhesive coating) to the pannus below the horizon of the panniculus. At this point in the application procedure, typically the panniculus is still being manually retracted. This central area of the top layer is used to initially position the top layer on the patient, and thus defines a positioning portion of the wound exposure device. In this step, the backing layer is still applied to the lower portion side panels 62, the central portion 22 and the upper portion 24 of the wound exposure device. Thus, although the film layer 12 of the wound exposure device is highly stretchable, because the backing layer is still applied to substantially all of the wound exposure device 10, the central (positioning) panel 64 of the lower portion 20 will not stretch significantly during application of the positioning panel 64 to the patient.

While the panniculus is still retracted, and the central panel of the lower portion 20 of the wound exposure device is adhered to the patient, one wing or lobe 34 of the lower portion 20 is folder over, its respective B-tab 68 is grasped, and the lower portion outer panel 62 of the backing layer is removed from the film or top layer 12 in the lower portion 20 to expose the adhesive of the film. As the backing layer is removed, the film is smoothed over the skin. This lobe of the lower portion 20 is now applied to the patients' skin and smoothed out. The lower portion outer panel 62 of the opposite side of the backing layer is then removed in the same manner, and the remaining portion of the lower portion 20 of the wound exposure device is adhered to the patient. The film 12 of the outer panels 62 can be stretched as may be necessary to apply the film to the patient.

At this point, the central portion 22 and top portion 24 still have their respective backing panels, and the lower portion 20 of the wound exposure device is fully adhered to the patient and has been smoothed out. At this point in the application process, the practitioner can discontinue manual retraction and allow the pannus to return to its natural state with the patient in supine position. The practitioner then folds back the central portion 22 over the lower portion 20, grasps one of the C-tabs 54, and removes the backing layer of the central or middle portion 22 from the top layer. As noted above, the film layer 12 is extremely stretchable (and can be stretched up to 500%). The backing layer is still applied to the upper portion 24 of the wound exposure device, and the lower portion 20 of the wound exposure device is applied to the patient. Thus, the only exposed portion of the film layer 12 is the middle portion 22. With the backing layer removed from the middle portion, the middle portion is stretched in a cephelad direction, for example, by holding onto the arms 38 of the upper portion 24 and pulling towards the patient's head. The middle portion 22 is stretched until the upper edge 42 of the upper portion 24 is approximately at the patient's thorax or throat. The middle portion 22 is then pressed against, and applied to the patient's skin. As can be appreciated, the central portion 22 will be adhered to the patient's chest. For a female patient, the side-to-side width or dimension of the central portion 22 is sized such that the central portion, when stretched, can fit between the patient's breasts. For example, prior to stretching, the central portion 22 can have a side-to-side width of about 8". At this point, retraction of the pannus is now complete.

After retraction has been completed, the upper portion 24 is folded over the middle portion 22 and the D-tab 86 is grasped to remove the upper portion central backing panel 84 from the top, film, layer 12 of the wound exposure device. This exposes the adhesive of the film layer 12 in the central area of the top portion 24. With the adhesive in the central area of the upper portion exposed, the central area of the upper portion is adhered to the patient's skin. When adhered, the top edge 42 will be in the area of the patient's collar bone (clavicle) or the jugular notch. This will position the top portion 24 of the retainer film 12. Thus, the central area of the body upper portion 24 defines a positioning area for the body upper portion 24. When the film of the upper portion central backing panel 84 is applied to the patient, the backing layer is still applied to the arms 38. Thus, the upper portion central backing panel 84 is not stretched significantly during application of the central section 84 to the patient.

With the wound exposure device film upper portion 24 secured in place, the arms 38 can be adhered to the patient. To do so, one of the arms 38 is folded over the central area of the upper portion, and its E-tab 88 is grasped and pulled away from the film layer to remove the upper portion backing panel 82 from that arm. This exposes the adhesive layer of the arm 38, and the arm 38 can then be applied to the patient's skin. As can be appreciated, due to the shape of the arm, the arm 38 will extend toward the patient's shoulder, and the edge 42 will partially encircle the patient's neck. The other arm is then adhered to the patient's skin in the same manner. When the backing panel of the arms 38 have been removed, the film layer 12 of the arms can be stretched as may be necessary to provide contact with the patient.

Once the wound exposure device film 12 has been fully applied to the patient, the film will support the patient's panniculus for an extended period of time such that the panniculus is supported away from the wound to prevent the wound from being covered by the panniculus, and to thus enable the wound to heal better. The top layer of the wound exposure device, as noted above, is made from a breathable, yet fluid resistant, material. Thus, air/gas can pass through the film, but fluids (water) cannot. Thus, the patient can bathe, generally as normal, when the film 12 is adhered to the patient's skin and is supporting the patient's panniculus away from the wound. The adhesive will enable the film to remain adhered to the patient for an extended period of time, typically for about 1 day to about 5 days.

In the description above, the retractor/stabilizer is removed prior to application of the wound exposure device 10. However, it may be easier to apply the wound exposure device 10 while the retractor/stabilizer is still in place and while the adipose tissue is already in a retracted position. For example, if the retractor/stabilizer disclosed in WO2014/120746 is used, the wound exposure device could be applied to the point where the wound exposure will maintain the adipose tissue in a retracted position (but not yet fully applied). At that point, the practitioners could start removing the retractor/stabilizer from the patient.

Modifications to the Wound Exposure Device

A modified wound exposure device 10' is shown in FIG. 2 overlaid with a retractor R from WO2014/120746 in which a lower portion of the retractor has been removed. The wound exposure device 10' is adapted in part to be used in conjunction with the retractor R. The wound exposure device 10' is generally similar to the wound exposure device 10. However, it has a shorter lower portion 20' and, concomitantly, a longer middle portion 22'. The upper portion 24' is generally the same as the upper portion 24 of the wound exposure device 10. Additionally, the lower back cut 50' is convexly arced (relative to the lower portion 20'). When the lower portion backing panels 62' and 64' are removed, the exposed lower portion of the film will have an arcuate upper edge which corresponds in shape to the lower edge of the retractor R, as seen, when the lower portion of the retractor R is removed. Thus, the lower portion of the wound exposure device can be applied to a patient while the retractor is still applied to the patient, and while the pannus is still held by the retractor R in a retracted position. Once the lower portion of the wound exposure device 10' has been applied to the patient's panniculus, the retractor R can be removed. While the retractor is being removed, the panniculus can be held in the retracted position using the wound exposure device. Once the retractor has been removed from the patient, the application of the wound exposure device 10' to the patient can be completed, as discussed above.

Once the wound has healed sufficiently, the film can be removed from the patient. The film is easily removed by peeling the film from the patient.

As noted above, the adhesive A which adheres the film 12 to the patient has an adhesive strength of about 19 oz/in. This is sufficient to hold the film 12 of the wound exposure device to the patient and maintain the patient's panniculus away from the incision site or wound site. Yet it not so strong that it will traumatize the patient's skin upon removal. Stated differently, the strength of the adhesive should be adequate to retain the wound exposure device in place for the duration of the wear time. However, the adhesive should permit atraumatic removal, i.e. without causing skin stripping (Rippon, White & Davies, Skin Adhesives and Their Role in Wound Dressings, Wounds UK, 2007 Vol. 3, No. 4, pp. 76-86). For example, the adhesive preferably has a strength greater than about 10 oz/in but less than about 50 oz/in.

Figure 3:
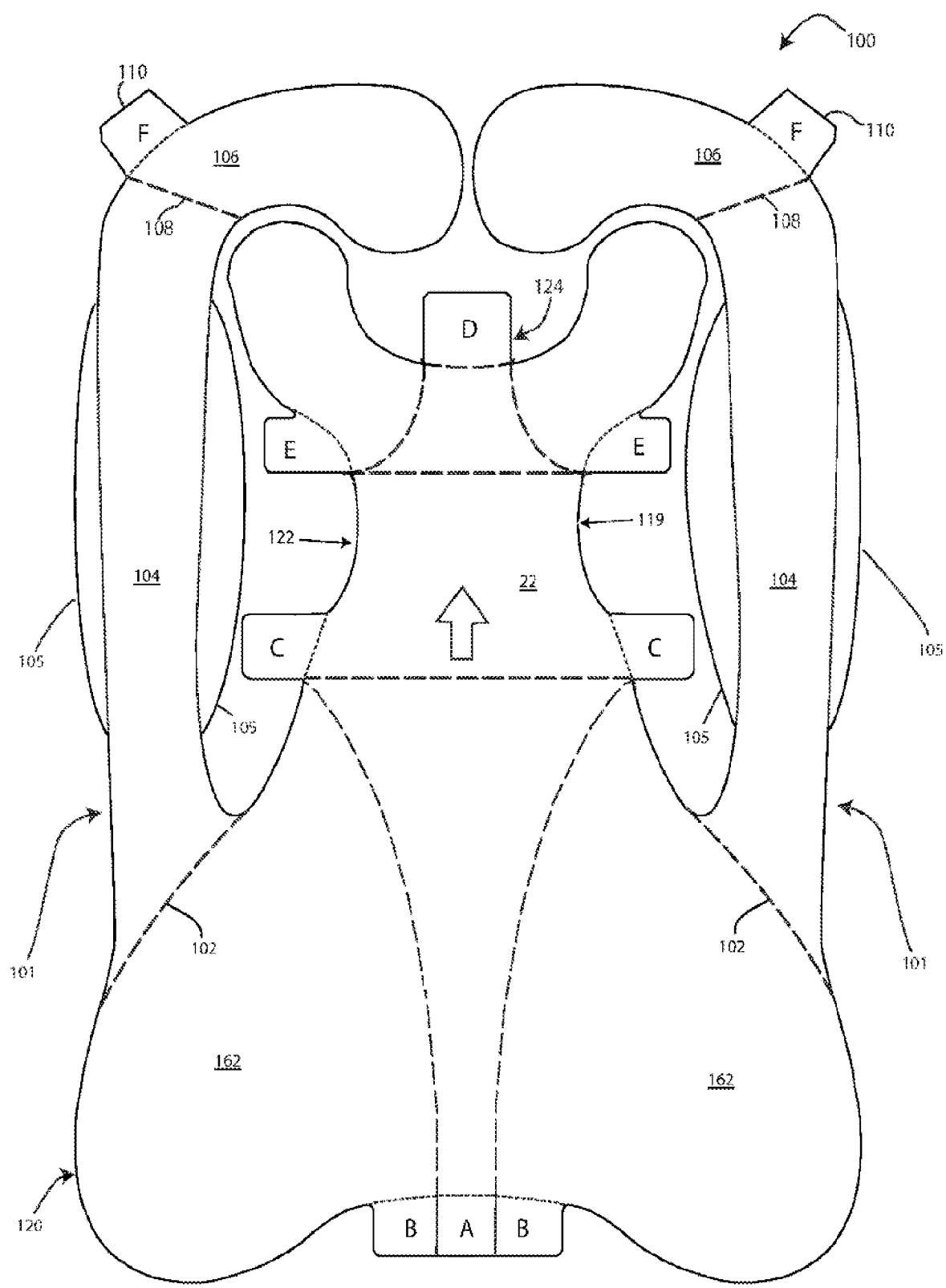
FIG. 3 is a plan view of a further variation of the wound exposure device wherein the device is provided with arms.
Figure 4:
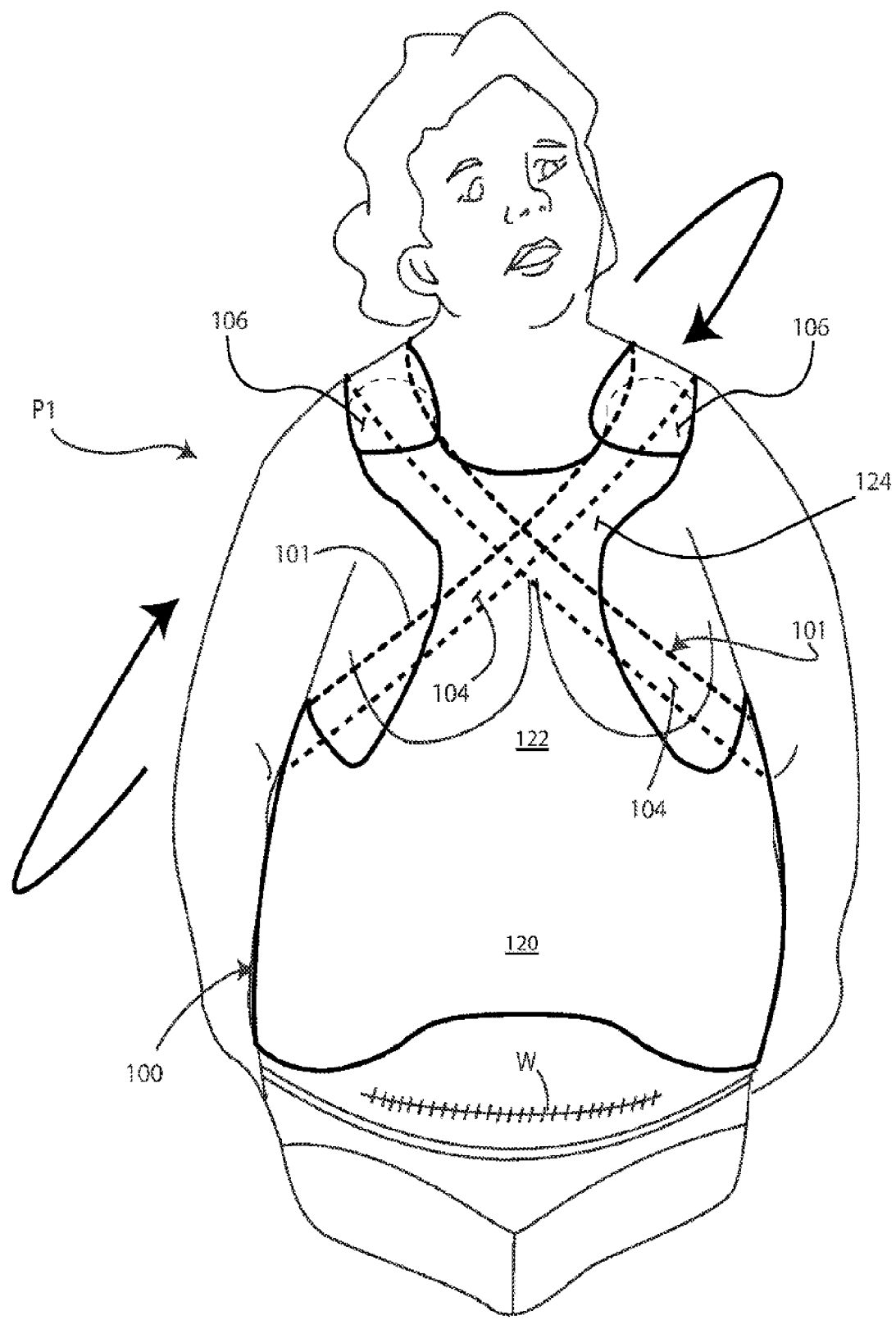
FIGS. 4 and 5 are front and side elevational views, respectively of the wound exposure device of FIG. 3 being worn by a patient.
Figure 5:
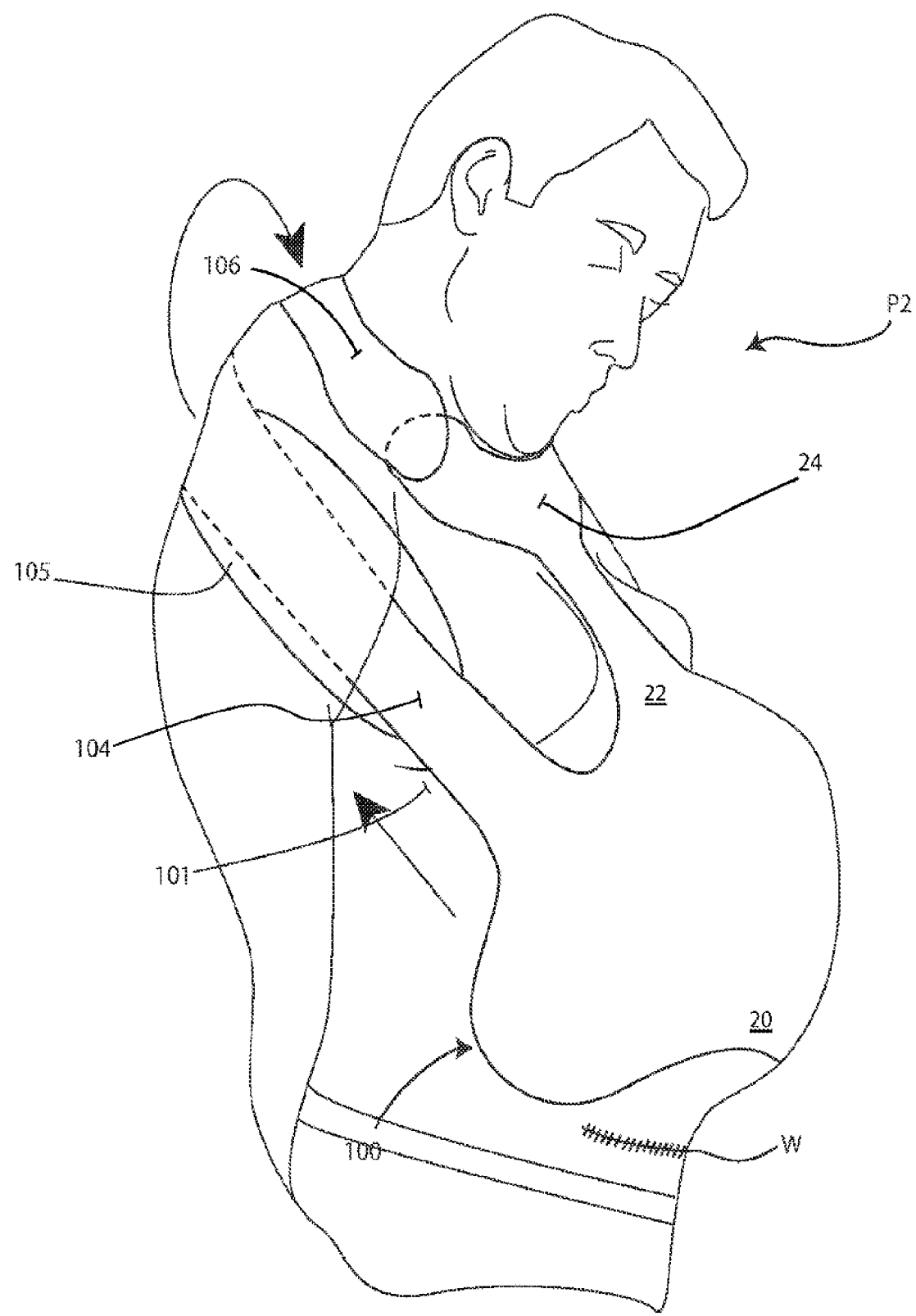

FIGS. 3-5 show an alternate wound exposure device 100. The wound exposure device 100 has a body 119 that is identical to the body 19 of the wound exposure device 10 (of FIG. 1). The body 119 includes a bottom portion 120, a middle portion 122 and an upper portion 124, identical to the corresponding portions 20, 22 and 24 of the body 19. The body 119 thus will not be further described.

The wound exposure device 100 adds arms 101 which extend from the upper edge of the side sections or lobes 162 of the lower portion 120 of the body 119. The backing of the arms 101 are separated from back panel of the lower portion 120 by means of back cuts 102, such that the film or upper layer of the arms 101 will remain with the upper layer of the body 119 of the wound exposure device 100 when the backing is removed from the arms 101. As shown in FIG. 3, the arms 101 each include a first portion 104 that extends from the body side panels 162. The first portions 104 of the arms 101 are shown to extend generally vertically (to be generally parallel to the machine direction of the film layer of the arms 101). This configuration facilitates manufacturing of the wound exposure device 100 (because the film from which the device is die-cut comes in predetermined widths) and allows for the arm portions 104 to stretch, as will be discussed below. The arm first portions 104 can include wings 105 which extend along a center length of the arm first portions 101 on opposite sides of each of the arms. These wings 105 are formed such that the backing stays with the wings when the backing is removed from the arms 101. This area of non-adhesive is intended to increase the comfort of the wound exposure device 100 when being worn.

The arm first portions 104 are not provided with tabs to remove the backing from the arms. When the arm first portions are stretched, after at least the bottom portion 120 of the wound exposure device 100 has been applied to the patient, the backing will automatically separate. Thus, tabs are not necessary for the arm first portions 104. However, tabs could be provided if desired.

In the wound exposure device 100, as die-cut, the arm portions 104 extend to the top of the yoke or upper portion 124. At the end of the arm first portions 104, the arms 101 each have a second portion 106 which extends inwardly above the top portion 124 of the body 119. The backing layer of the arm second portions 106 are separated from the backing layer of the first portions 104 by a back cut 108. Thus, when the backing layer is removed from the arm first portions 104, the backing layer will remain with the arm second portions 106. A tab 110 (labeled "F") is associated with each arm second portion 106 to remove the backing layer from the arm second portion 106.

Application of the wound exposure device 100 is generally similar to application of the wound exposure device 10. If the wound exposure device 100 is applied to the patient while the patient is generally prone (or otherwise on their back), the body 100 is applied to the patient identically as described above. After the body 119 has been applied to the patient, the patient is moved to a sitting or standing position. At that point, the arms 101 are applied to the patient. FIGS. 4 and 5 show two different ways to apply the arms.

With respect to FIG. 3, one of the arms 101 is held by its second portion 106 and pulled to stretch the arm first portion. As the arm first portion 104 is stretched, the backing layer will separate or delaminate from the top layer of the arm first portion 104. The arm second portion 106 is not stretched at this time, and thus the backing layer of the arm second portion remains with the arm second portion. As the backing layer of the arm first portion separates or delaminates from the top layer of the arm first portion, the backing layer can be grabbed and removed from the top layer of the arm first portion to complete the removal of the backing layer from the arm first portion 104. With reference to FIG. 4, this arm first portion is then stretched to extend diagonally and upwardly across the patient's back, such that the arm second portion is over the opposite shoulder. Thus, for example, the arm first portion 104 of the left arm 101 is stretched such that its second portion 106 extends over the patient's right shoulder to reach over the top of the upper portion 124 of the body 119. When the arm first portion 104 is sufficiently stretched, the arm first portion is adhered to the patient. The backing for the arm second portion 106 is then removed, and the arm second portion 106 will reach over the patient's opposite shoulder to be adhered to the top of the upper portion 124 of the body 119. After the first arm is applied, the second arm 101 is then applied in the same fashion.

With respect to FIG. 5, the backing layer of one of the arms 101 is removed from its arm first portion 104. This arm first portion is then stretched to extend under the patient's armpit, and then to come up and over the same shoulder. Thus, for example, the first portion 104 of the left arm 101 is stretched such that its second portion 106 can extend over the patient's left shoulder to reach over the top of the upper portion 124 of the body 119. When the arm first portion 104 is sufficiently stretched, the arm first portion is adhered to the patient. The backing for the arm second portion 106 is then removed, and the second portion 106 will reach over the patient's same-side shoulder to be adhered to the top of the upper portion 124 of the body 119. After the first arm is applied, the second arm 101 is then applied in the same fashion. In FIG. 4, the arms 101 are applied to cross each other on the patient's back. In FIG. 5, on the other hand, the arms do not cross, and remain on the same side of the patient. The decision as to how to apply the arms will be made on a case-by-case basis. However, it is noted that the patients (P1, P2) of FIGS. 4 and 5, respectively, who are shown to have different sized panniculi, with patient P2 (FIG. 5) having a larger panniculus. For the arms to cross behind the patient (as in FIG. 4) may require more stretching than for the arm to remain on the same side of the patient (as in FIG. 5). Thus, in a patient with a larger panniculus, the method as shown in FIG. 5 may be more desirable. In both figures, the wound exposure device 100 is shown to hold the patient's panniculus off of an incision or other wound W. In the absence of the wound exposure device 100 (or 10 or 10'), the patient's panniculus would cover the wound W, thereby interfering with healing of the wound. Because the wound exposure device exposes the wound W, the wound can be more properly cared for, and can heal more normally.

By providing the arms 100, which adhere to the upper portion of the body 119, downward forces applied to the wound exposure device by the weight of the panniculus are transferred from the patient's chest area (which could create some shear forces on the patient's skin) to the patient's shoulders. This would reduce the shear forces that would otherwise be applied to the skin at the patient's chest and generate compression forces which are better borne by the patient's shoulders. The provision of the arms 101 may thus make the wound exposure device more comfortable for the patient to wear.

Figure 6:
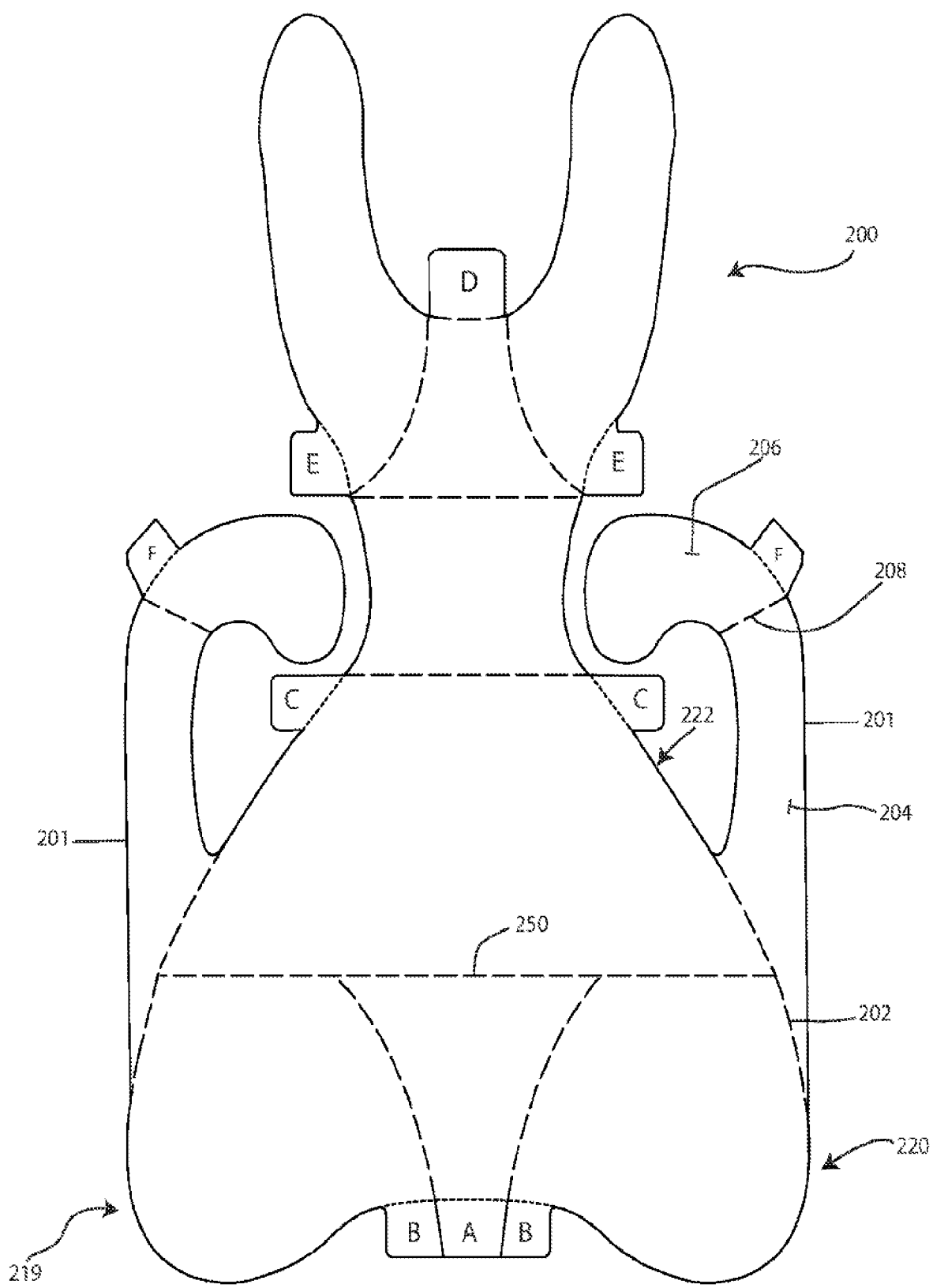
FIG. 6 is a plan view of a wound exposure device similar to that of FIG. 3, but with shorter arms.

An alternate armed wound exposure device 200 is shown in FIG. 6. The wound exposure device 200 includes a body 219 which is based on the body 19' of the wound exposure device 10' of FIG. 2. Thus, the wound exposure device has a short lower portion 220 and a longer central portion 222. However, the body 291 of the wound exposure device 200 differs from the body of the wound exposure device 10' in that the lower back cut 250 which separates to backing lower portion 220 from the backing central portion 222 is straight, rather than arced. As with the wound exposure device 100, the wound exposure device 200 includes a pair of arms 201 having a first portion 204 and a second portion 206. As seen, the base or root of the arms 201 spans (or is bisected by) the lower back cut 250. The backing of the arms 201 is separated from the backing of the body 219 by a back cut 202, and the backing of the first and second portions of the arms are separated by a back cut 208. The arms 201 are shorter than the arms 101 of the wound exposure device 100. The wound exposure device 200 would be applied in the same manner as the wound exposure device 10' or 100, expect that the arms 201 will wrap around the patient's body, to be more like a belt than suspenders.

Figure 7:
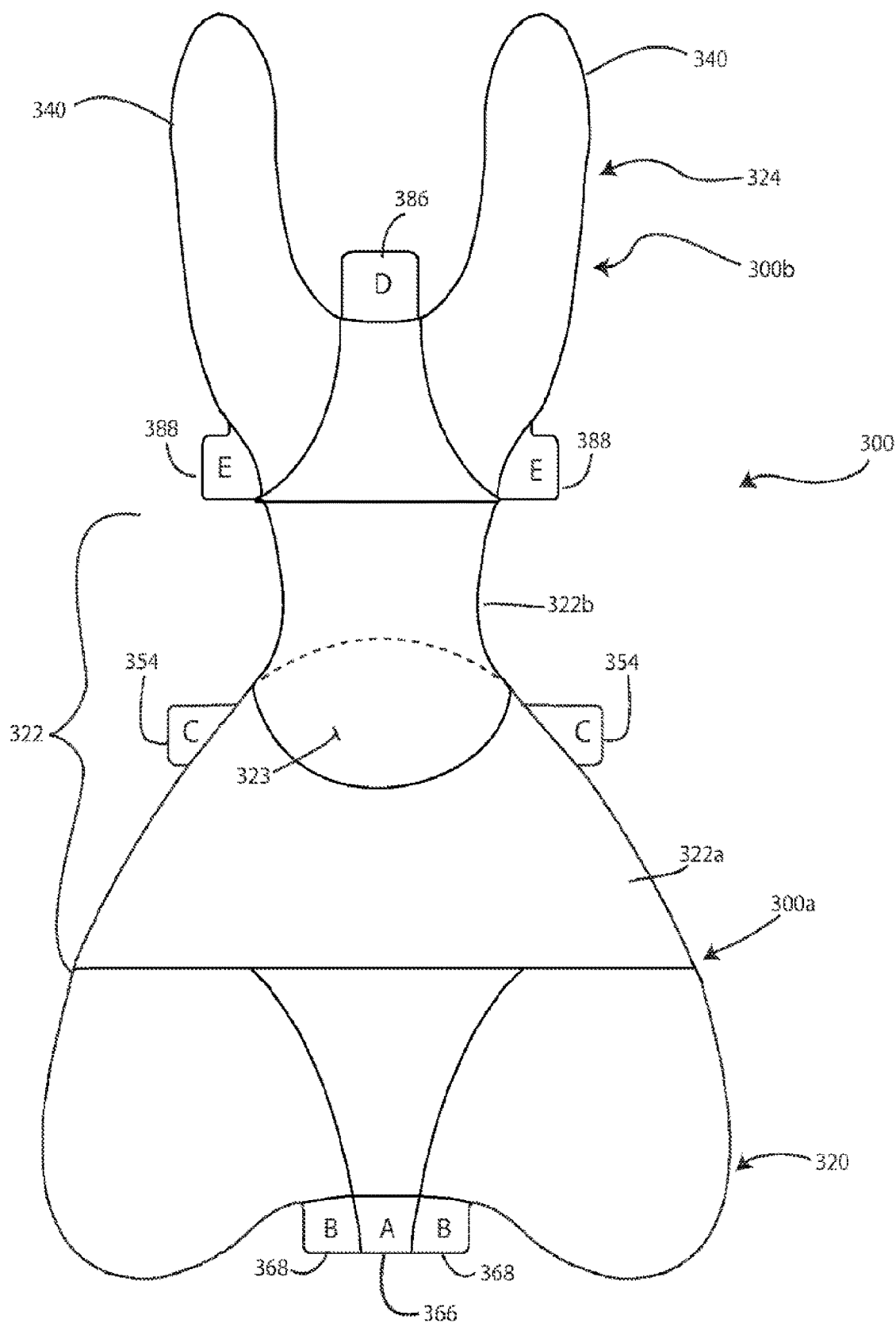
FIG. 7 is a plan view of an assembled 2-piece wound exposure device.
Figure 8:
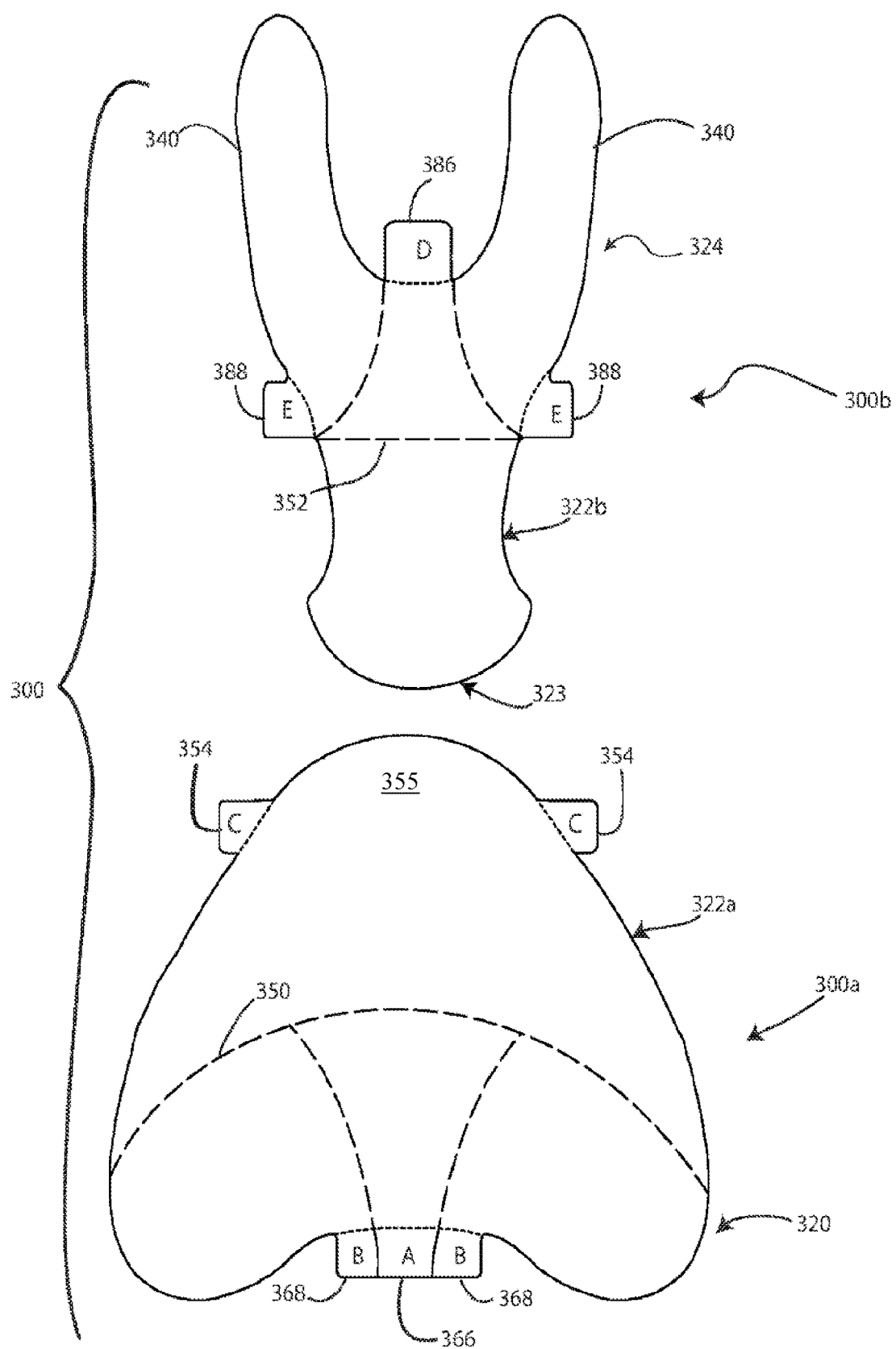
FIG. 8 is an exploded plan view of the 2-piece wound exposure device.

FIGS. 7-8 show a third embodiment 300 of the wound exposure device. The wound exposure device 300 is a two-part or two-piece wound exposure device and is comprised of a lower piece 300a and an upper piece 300b. The lower piece 300a defines the lower portion 320 and a lower part 322a of the middle portion 322 of the completed wound exposure device. The back cut 350 separating the lower portion 320 from the middle lower part 322a is shown to be arced (as with the wound exposure device 10'). However, the back cut 350 could be formed as a straight line (as with the wound exposure device 10). The lower piece 300a is shown to be generally triangular, with a concave bottom edge, rounded lower corners, and a rounded apex. A-tab 366 and B-tabs 368 are provided for along the bottom edge of the lower piece 300a to facilitate removal of the backing from the lower portion 320, in the same way as described with the wound exposure device 10. C-tabs 354 are provided slightly below the apex of the lower piece to facilitate removal of the backing panel of the lower middle portion 322a. The apex of the lower piece 300a is above the top edges of the C-tabs, and can define a holding or grasping area 355 if desired. In such a case, a back cut would be provided in the top panel extending between the top edges of the C-tabs. This cut would enable the backing panel to remain with the top layer when the remainder of the backing panel for part 322a is removed using the C-tabs. This holding area or grasping 355 would enable a practitioner to handle or grasp the top of the lower piece 300a without contacting adhesive of the lower piece film.

The upper piece 300b includes the top part 322b of the middle portion 322 of the completed wound exposure device 300 and the yoke or upper section 324 of the wound exposure device. The middle top part 322b is elongate with concave side edges and a convexly curved bottom edge. A top back cut 352 separates the middle top part 322b from the yoke 324. The yoke 324 corresponds to the yoke or top portion 24 of the wound exposure device 10. The yoke 324 includes arms 340 which extend out from a central portion. E-tabs 388 are provided to facilitate removal of the backing layer from the arms 340, and a D-tab 386 is provided at the top of the yoke 324 between the arms 340 to facilitate removal of the backing layer from the middle portion or body of the yoke. No tab is provided for the middle top part 322b (which forms the lower part of the top piece 300b). The backing layer of the middle top part 322b is separated from the film by stretching the top layer. As described above in conjunction with the arms of the wound exposure device 100, as the middle top part 322b is pulled or stretched, the backing layer of the middle top part will automatically delaminate from the film or top layer of the middle top part. However, if desired, tabs could be provided to facilitate removal of the backing layer from the middle top part 322a.

In use, the lower piece 300a is applied to the patient first. After the pannus has been retracted, the upper piece 300b is applied to the lower piece 300a. As seen in FIG. 7, the curved portion of the upper piece 300b defines a tongue 323 which is adhered to the upper portion of the lower piece 300a. Either the lower piece can overlie the upper piece, or the upper piece can overlie the lower piece.

In an alternative method of applying the wound exposure device 300 to the patient, the upper piece and lower piece can be adhered together to form a complete wound exposure device. This complete wound exposure device would then be applied to the patient as discussed above. However, this alternative method would require earlier removal of the backing layer of either the middle lower part 322a or the middle upper part 322b.

Figures 9, 9A:
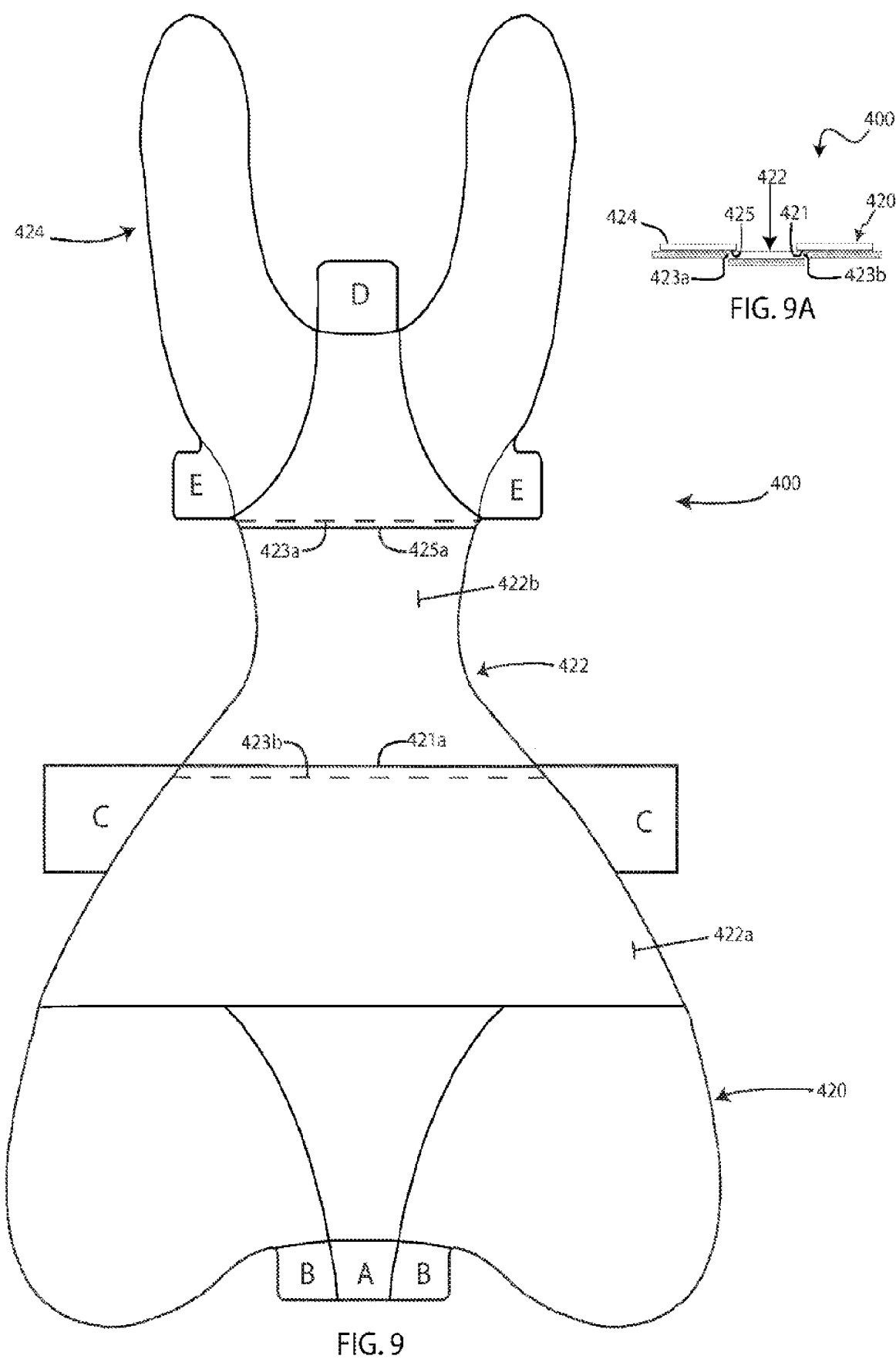
FIG. 9 is a plan view of an assembled 3-piece would exposure device.
FIG. 9A is an exploded side elevational view (on a reduced scale relative to FIG. 9) of the 3-piece wound exposure device.

The wound exposure device could also be provided as a three piece assembly. Such a three-piece wound exposure 400 device is shown in FIGS. 9 and 9A, and includes a lower piece 420, a middle piece 422, and an upper piece 424. The lower piece 420 is substantially similar to the lower piece 300a of the wound exposure device 300, and thus includes a lower portion 422a of the middle section, when the assembled 3-piece wound exposure device is compared to the 1-piece wound exposure device of FIG. 1, for example. The upper piece 424 defines the yoke 324. The middle piece 422, when compared to the 1-piece wound exposure device, defines an upper middle portion 422b of the assembled wound exposure device. In FIG. 9, the top and bottom edges 423a,b of middle piece 422 are defined by dotted lines. The bottom of the top piece 424 and the top of the bottom piece 420 define lips 425, 421, respectively, which overlap the top and bottom edges, respectively, of the middle section 422 in the assembled wound exposure device. This can be seen in FIG. 9, where the bottom edge 425a of the top piece and the top edge 421a of the bottom piece overlap the top and bottom edges, respectively, of the middle piece.

Providing for a third piece (which defines the middle portion, or the middle top part 322b) allows for freedom in selection of materials for the middle portion or the middle top part, as the case may be. It is preferred that this third piece be stretchable. However, it need not be adhesive. Thus, the middle piece 422 can be made from a breathable tape which has no adhesive, such as Product No. 9832F which is available from 3M. Further, the middle piece 422 can be made from a stretch fabric, such as Lycra® or Spandex®, or a blend that includes stretch fibers, to potentially make the wound exposure device more comfortable to wear for extended periods of time. Additionally, the middle piece can be made in a variety of lengths to accommodate different sized panniculi. Thus, a hospital can stock the upper and bottom pieces (which would all be of one sized) and a plurality of sized of middle pieces. In this three-piece version, the top and bottom pieces, which need not be as stretchy as the middle piece, could be made from a material which is less stretchy than the middle piece. Further, the top and/or bottom pieces could be made from a substantially non-stretchy material (i.e., with a stretchability of less than 10%) Thus, the three-part wound exposure device can have its three pieces made from different materials.

In the case of the three-piece wound exposure device, the top part of the lower piece would overlie the middle piece, and the lower part of the top piece would overlie the middle piece, as seen in FIG. 9A. The pieces of the three-part wound exposure device could be assembled together prior to application of the wound exposure device to the patient. Alternatively, the three-piece wound exposure device could be assembled together as the device is applied to the patient.

The wound exposure device 10, 10', 100, 200, 300, 400 can be worn for extended periods of time, as discussed above. The wound exposure device also allows for certain post-operative out-patient procedures. For example, because the wound exposure device retains the panniculus or other excess flesh away from the wound, in the manner of a retractor, the wound exposure device allows, for example, for a subfacia pain pump to be implanted, if necessary. This, as can be appreciated, will allow the patient to help control his/her pain. The wound exposure devices can be hemmed to provide for a glue- or adhesive-free perimeter to the wound exposure device. In addition, the wound exposure device is printable, foldable and sterilizable. It is intended to be used only a single time.

As various changes could be made in the above constructions without departing from the scope of the claimed invention, it is intended that all matter contained in the above description or shown in the accompanying drawings shall be interpreted as illustrative and not in a limiting sense. For example, the locating panel 64 of the lower portion could be defined by a single back cut which begins and ends at the bottom edge 72. In this instance, the side panels would be connected to each other between the locating panel 64 and the lower cut 50 at the top of the bottom portion 20. This would allow for the backing panel of the lower portion to be removed in two parts, rather than three parts. The film layer 12 of the wound exposure device is stretchable. However, it need not have a stretchability as great as 500%. Preferably, the film 12 has a strechability of at least 50%.

The top layer of the wound exposure device 100 (FIG. 3) could be made from a woven material, rather than an elastomeric material. Woven materials do not stretch to the same extent as elastomeric materials, thus, such a wound exposure device would need to be provided in different sizes. To enable a woven top layer to expand; the material for the wound exposure device could be cut at a 45° angle to the machine direction of the top layer. Although hook-and-pile (such as Velcro®) can be used to connect the arms of the woven top layer to the upper portion of the woven top layer, it is still preferable to rely on adhesive. Finally, any of the one-piece wound exposure devices could be formed as multi-piece would exposure devices. In addition, the armed versions of the wound exposure device (FIGS. 3 and 6) could be made without arms, and the armless versions (FIGS. 1, 2, and 7) could be made with arms. These examples are merely illustrative.

The invention claimed is:

1. A multi-ply adhesive wound exposure device formed from a single sheet of two-ply material having a top layer and a backing layer; the top layer having an adhesive applied to a surface of the top layer facing the backing layer to removably adhere the top layer and backing layer together; the top layer being made from a stretchable material and the backing layer being made from a material which is substantially not stretchable; the multi-ply adhesive wound exposure device comprising:
an elongate body having a top edge, a bottom edge, and opposed side edges; said elongate body comprising a bottom portion, a central portion and an upper portion; the bottom, central, and upper portions being separated from each other by upper and lower back cuts in the backing layer which divide the backing layer into a lower portion backing panel, a central portion backing panel and an upper portion backing panel;
said upper portion being generally U-shaped and comprising a pair of side arms defined in part by said top edge, said top edge defining a concave curve, whereby said upper portion defines a generally U-shaped yoke, wherein the concave curve of said top edge is sized such that each arm of said pair of side arms is configured to extend along an opposite side of a neck of a patient when the multi-ply adhesive wound exposure device is applied to the patient;
at least one tab associated with each of the bottom, central, and upper portions of said elongate body; each at least one tab being defined in part by a face cut in the top layer which separates the top layer of the at least one tab from the top layer of the elongate body, such that when the at least one tab is pulled away from the top layer, a backing panel associated with the at least one tab is removed from the top layer.

2. The multi-ply adhesive wound exposure device of claim 1 further comprising two arms, said arms extending from opposite sides of said elongate body.

3. The multi-ply adhesive wound exposure device of claim 2 wherein said arms each comprise a first arm portion which extends in a direction generally parallel to a machine direction of the material of said top layer to be as stretchable as said top layer and a second arm portion which is not generally parallel to the machine direction of the material of said top layer.

4. The multi-ply adhesive wound exposure device of claim 3 wherein the backing layer of the second arm portion is separated from the backing layer of the first arm portion by a back cut.

5. The multi-ply adhesive wound exposure device of claim 4 wherein said second arm portion comprises a tab associated with the backing layer of said second arm portion to facilitate removal of said backing layer of said second arm portion.

6. The multi-ply adhesive wound exposure device of claim 2 wherein each of said arms includes a wing extending along an opposite side of at least a portion of each of said arms to provide a segment of increased width for each of said arms.

7. The multi-ply adhesive wound exposure device of claim 4 wherein said second arm portion lacks a tab.

8. The multi-ply adhesive wound exposure device of claim 1 wherein the top layer is comprised of a material that has an elongation factor of at least 50% in a machine direction of the material.

9. The multi-ply adhesive wound exposure device of claim 8 wherein the top layer is formed from a thermoplastic elastomer.

10. The multi-ply adhesive wound exposure device of claim 9 wherein the thermoplastic elastomer is formed from one or both of polyester and polyurethane.

11. The multi-ply adhesive wound exposure device of claim 8 wherein the top layer is comprised of a material that can be stretched up to 500% in the machine direction.

12. The multi-ply adhesive wound exposure device of claim 8 wherein the top layer has a thickness of about 1 mil to about 5 mils.

13. The multi-ply adhesive wound exposure device of claim 1 wherein said lower portion backing panel has at least a first back cut extending from said lower back cut to the bottom edge of said elongate body to divide the lower portion backing panel into at least first and second backing layer panels, said device comprising a tab associated with each of said first and second backing layer panels.

14. The multi-ply adhesive wound exposure device of claim 13 wherein said bottom portion includes a second back cut extending from the lower back cut to the bottom edge to define a third backing layer panel; said multi-ply adhesive wound exposure device comprising a tab associated with said third backing layer panel; two of said first, second, and third backing baking layer panels being side panels and one of said first, second and third backing layer panels being a central panel between said side panels.

15. The multi-ply adhesive wound exposure device of claim 14 wherein said first and second back cuts in said bottom portion extend from ends of said lower back cut to a point on said bottom edge proximate a center of said bottom edge, such that the central panel has an upper edge defined by said lower back cut which is longer than a lower edge defined by said bottom edge of said elongate body.

16. The multi-ply adhesive wound exposure device of claim 13 wherein said lower back cut defines either a generally straight line or an upwardly extending generally arcuate line.

17. The multi-ply adhesive wound exposure device of claim 1 wherein said upper portion backing panel has at least a first upper portion back cut extending from said upper back cut to an upper edge of said elongate body to divide the upper portion backing panel into first and second upper portion backing layer panels, said device comprising a tab associated with each of said first and second upper portion backing layer panels.

18. The multi-ply adhesive wound exposure device of claim 17 wherein said upper portion includes a second upper portion back cut extending from the upper back cut to an upper edge of said elongate body to define a third upper portion backing layer panel; said device comprising a tab associated with said third upper portion backing layer panel; said first and second upper portion backing layer panels defining upper portion side or arm panels and said third upper portion backing layer panel defining an upper portion central panel between said upper portion side or arm panels.

19. The multi-ply adhesive wound exposure device of claim 18 wherein said first and second upper portion back cuts extend from ends of said upper back cut to a point on said upper edge of said elongate body proximate a center of said upper edge of said elongate body, such that the third upper portion panel has an upper edge defined by said upper edge of said elongate body which is shorter than a lower edge defined by said upper back cut in said backing layer.

20. The multi-ply adhesive wound exposure device of claim 1 wherein the adhesive has an adhesive strength configured to be sufficiently low so as to substantially prevent trauma to human skin when the multi-ply adhesive wound exposure device is removed from the human skin.

21. The multi-ply adhesive wound exposure device of claim 20 wherein the adhesive has a strength of about 10 oz/in to about 50 oz/in.

22. The multi-ply adhesive wound exposure device of claim 1 wherein each arm of the pair of side arms is sized to extend around the neck of the patient to a scapula of the patient when the multi-ply adhesive wound exposure device is applied to the patient.

23. The multi-ply adhesive wound exposure device of claim 1 wherein said at least one tab is an outboard tab which extends from the elongate body of said multi-ply adhesive wound exposure device.

24. The multi-ply adhesive wound exposure device of claim 1 wherein the top layer has a machine direction which extends from top-to-bottom of the multi-ply adhesive wound exposure device.

25. The multi-ply adhesive wound exposure device of claim 1 where in the top layer has a machine direction which extends from side-to-side of the multi-ply adhesive wound exposure device.

26. A wound exposure device comprising:
an elongate body having a top edge, a bottom edge, and opposed side edges; said elongate body comprising an upper portion defined in part by said top edge, a middle portion below said upper portion, and a bottom portion below said middle portion; said bottom portion being defined in part by said bottom edge; said middle portion having a side-to-side width less than a side-to-side width of either said upper portion or said bottom portion; said upper portion being generally U-shaped and comprising a pair of side arms defined in part by said top edge, said top edge defining a concave curve, whereby said upper portion defines a generally U-shaped yoke, wherein the concave curve of said top edge is sized such that each arm of said pair of side arms is configured to extend along an opposite side of a neck of a patient when the wound exposure device is applied to the patient;
at least said upper and bottom portions comprising a top layer and a backing layer; the top layer having an adhesive applied to a surface of the top layer facing the backing layer to removably adhere the top layer and backing layer together;
at least the middle portion being made from a stretchable material.

27. The wound exposure device of claim 26 wherein said wound exposure device comprises an upper piece defining said generally U-shaped yoke and a bottom piece defining said bottom portion.

28. The wound exposure device of claim 27 wherein said wound exposure device is a three-piece assembly, and wherein said wound exposure device further includes a middle piece defining at least a top part of said middle portion.

29. The wound exposure device of claim 28 wherein the middle piece is made from a different material than either or both of the upper and bottom pieces.

30. The wound exposure device of claim 29 wherein the upper and bottom pieces are made from the same material.

31. The wound exposure device of claim 27 wherein said wound exposure device is a two-piece assembly, and wherein said upper piece further defines an upper part of said middle portion and said bottom piece further defines a lower part of said middle portion.

32. The wound exposure device of claim 28 wherein said middle piece is formed from a one-ply material which is non-adhesive.

33. The wound exposure device of claim 28 wherein said upper piece and said bottom piece are substantially non-stretchable.

34. The wound exposure device of claim 26 wherein the pair of side arms of the generally U-shaped yoke extend from a central portion of the generally U-shaped yoke; each arm of the pair of side arms of the generally U-shaped yoke having a length such that each arm of the pair of side arms will extend around the neck of the patient to a scapula of the patient when the wound exposure device is applied to the patient.

35. The wound exposure device of claim 26 including at least one tab associated with each of the upper and bottom portions; each at least one tab being defined in part by a face cut in the top layer which separates the top layer of the at least one tab from the top layer of the elongate body, such that when the at least one tab is pulled away from the top layer, a backing panel associated with the at least one tab is removed from the top layer.

36. The wound exposure device of claim 26 wherein said wound exposure device is formed from a single sheet of two-ply material.

37. The wound exposure device of claim 26 wherein the adhesive has an adhesive strength configured to be sufficiently low so as to substantially prevent trauma to human skin when the wound exposure device is removed from the human skin.

38. A method of applying a wound exposure device to a patient to support and maintain redundant/excess tissue away from a wound to facilitate healing of the wound; the wound exposure device comprising a body having a top portion, a middle portion, and a bottom portion; at least said top and bottom portions of the body comprising a top layer and a backing layer; said top layer having an adhesive applied to a surface of the top layer facing said backing layer to removably adhere said backing layer to the top layer, the backing layer being made from a substantially non-stretchable material; at least the middle portion of the body being made from a material stretchable in a machine direction of the material; at least one tab associated with each of the top and bottom portions of said body; each at least one tab being defined in part by a face cut in the top layer which separates the top layer in the at least one tab from the top layer in the body, such that when the at least one tab is pulled away from the top layer, the backing layer associated with the at least one tab is removed from the top layer; the method comprising:
a) manually retracting the redundant/excess tissue away from the wound and in a cephalad direction;
b) removing the backing layer from the bottom portion of the body and applying the top layer of the bottom portion of the body to the redundant/excess tissue;
c) removing the backing layer from a central panel between arms of said top portion of said body after the bottom portion of said top layer has been applied to the patient;
d) while the backing layer is still adhered to the arms of the top portion of the body and while still manually retracting the redundant/excess tissue, stretching the middle portion of the body until a top edge of the wound exposure device is proximate a clavicle or jugular notch of the patient and then securing the central panel of the wound exposure device to the patient;
e) removing the backing layer from the top portion of the wound exposure device and applying the top portion of the top layer to the patient.

39. The method of claim 38 wherein the step of removing the backing layer from the top portion of the body of the wound exposure device comprises:
e1) removing a first portion of the backing layer of the top portion of the body to expose a positioning area of the top layer of the top portion and adhering the positioning area to the patient proximate the clavicle or jugular notch of the patient and then securing the positioning area of the wound exposure device to the patient;
e2) then removing a remainder of the backing layer of the top portion to expose the adhesive of the top layer of a remainder of the top portion and adhering the remainder of the top layer of the top portion to the patient.

40. The method of claim 39 wherein said first portion of the backing layer of the top portion that is removed in step (e1) exposes a portion of the adhesive of the top layer in a central area of the top layer of the top portion, whereby the backing layer of the top portion comprises a central panel and two side panels; said step of removing the remainder of the backing layer of said top portion comprising (1) removing the backing layer from a first of said side panels and adhering said top layer of said first of said side panels to said patient, and (2) removing the backing layer from a second of said side panels and adhering said top layer of said second of said side panels to said patient.

41. The method of claim 40 wherein said wound exposure device further comprises two arms, said arms extending from each of opposite sides of said body; each of said arms comprising a first arm portion which extends in a direction generally parallel to the machine direction of the material of said top layer to be as stretchable as said top layer and a second arm portion which is not generally parallel to the machine direction of the material of said top layer; the backing layer of the second arm portion being separated from the backing layer of the first arm portion by a back cut; said method further comprising:
(f) adhering the top layer of each of said arms to said patient such that said arms extend along at least a portion of a back of the patient and over a shoulder of said patient, such that the second arm portion can be adhered to said top portion of said body.

42. The method of claim 41 wherein said step (f) of adhering the top layer of each of said arms to said patient comprises:
(f1) removing the backing layer from said first arm portion and stretching said first arm portion until said second arm portion can be positioned to be adhered to said top portion of said body with said first arm portion extending along at least a portion of the back of the patient;
(f2) adhering said first arm portion to said patient;
(f3) removing the backing layer from said second arm second portion; and
(f4) adhering said second arm portion to said patient and to said top portion of said body.

43. The method of claim 42 wherein said step of stretching said first arm portion comprises stretching said first arm portion such that said first arm portion remains on one side of the patient's body.

44. The method of claim 42 wherein said step of stretching said first arm portion comprises stretching said first arm portion such that said first arm portion crosses behind the patient such that each of said arms extends diagonally upwardly and over an opposite shoulder.

45. The method of claim 38 wherein the step of removing the backing layer from the bottom portion of the body of the wound exposure device comprises:
- b1) removing a first portion of the backing layer of the bottom portion of the body to expose a positioning area of the top layer of the bottom portion and adhering the positioning area to the redundant/excess tissue;
- b2) then removing a remainder of the backing layer of the bottom portion to expose the adhesive of the top layer of a remainder of the bottom portion and adhering the remainder of the bottom portion of the top layer to the redundant/excess tissue.

46. The method of claim 45 wherein said first portion of the backing layer of the bottom portion that is removed in step (b1) exposes a portion of the adhesive of the top layer in a central area of the top layer of the bottom portion, whereby the backing layer of the bottom portion of the body comprises a central panel and two side panels; said step of removing a remainder of the backing layer of said bottom portion of said body comprising (1) removing a first of said side panels and adhering said top layer corresponding to said first of said side panels to the redundant/excess tissue and (2) removing a second of said side panels and adhering said top layer corresponding to said second of said side panels to the redundant/excess tissue.

\* \* \* \* \*